US008926746B2

(12) United States Patent
Wakamiya

(10) Patent No.: US 8,926,746 B2
(45) Date of Patent: Jan. 6, 2015

(54) FLAKY PARTICLES AND LUSTER PIGMENT, AND COSMETIC, COATING COMPOSITION, RESIN COMPOSITION AND INK COMPOSITION EACH CONTAINING THE SAME

(75) Inventor: Takashi Wakamiya, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 722 days.

(21) Appl. No.: 12/225,907

(22) PCT Filed: Apr. 3, 2007

(86) PCT No.: PCT/JP2007/057484
§ 371 (c)(1),
(2), (4) Date: Oct. 1, 2008

(87) PCT Pub. No.: WO2007/114442
PCT Pub. Date: Oct. 11, 2007

(65) Prior Publication Data
US 2009/0274735 A1 Nov. 5, 2009

(30) Foreign Application Priority Data

Apr. 5, 2006 (JP) ................................. 2006-104509
Oct. 12, 2006 (JP) ................................. 2006-278656

(51) Int. Cl.
| C09C 1/00 | (2006.01) |
| C09D 11/00 | (2014.01) |
| C09D 1/00 | (2006.01) |
| A61Q 1/02 | (2006.01) |
| A61K 8/25 | (2006.01) |
| C03B 37/005 | (2006.01) |
| C09D 5/36 | (2006.01) |
| C09D 7/12 | (2006.01) |
| C09D 11/037 | (2014.01) |
| A61K 8/02 | (2006.01) |
| A61K 8/81 | (2006.01) |
| A61Q 1/06 | (2006.01) |
| A61Q 1/10 | (2006.01) |
| A61Q 3/02 | (2006.01) |
| C08K 3/40 | (2006.01) |
| C08K 9/02 | (2006.01) |

(52) U.S. Cl.
CPC ... *A61Q 1/02* (2013.01); *A61K 8/25* (2013.01); *C03B 37/005* (2013.01); *C09C 1/0018* (2013.01); *C09C 1/0021* (2013.01); *C09C 1/0078* (2013.01); *C09D 5/36* (2013.01); *C09D 7/1283* (2013.01); *C09D 7/1291* (2013.01); *C09D 11/037* (2013.01); *A61K 8/0254* (2013.01); *A61K 8/8147* (2013.01); *A61K 2800/43* (2013.01); *A61Q 1/06* (2013.01); *A61Q 1/10* (2013.01); *A61Q 3/02* (2013.01); *C01P 2004/51* (2013.01); *C01P 2006/62* (2013.01); *C08K 3/40* (2013.01); *C08K 9/02* (2013.01); *C09C 2200/102* (2013.01); *C09C 2200/1025* (2013.01); *C09C 2200/301* (2013.01); *A61K 2800/412* (2013.01); *A61K 2800/621* (2013.01); *A61K 2800/624* (2013.01); *A61K 2800/651* (2013.01)
USPC ...................... 106/415; 106/31.65; 106/286.1

(58) Field of Classification Search
USPC .......................................... 106/415, 482, 489
See application file for complete search history.

(56) References Cited

U.S. PATENT DOCUMENTS

| 6,579,355 B1 * | 6/2003 | Schmidt et al. ............... 106/415 |
| 2002/0169244 A1 | 11/2002 | Ostertag et al. |
| 2003/0027919 A1 | 2/2003 | Fritz |

(Continued)

FOREIGN PATENT DOCUMENTS

| DE | 101 14 446 | 9/2002 |
| JP | 62-175045 U | 11/1987 |

(Continued)

OTHER PUBLICATIONS

Ito, Seijiro, ed., "Ganryo no Jiten" (Dictionary of Pigments), First edition, Asakura Publishing Co., Ltd., pp. 232-234, 239-241, Sep. 25, 2000.

(Continued)

*Primary Examiner* — Shuangyi Abu Ali
(74) *Attorney, Agent, or Firm* — Hamre, Schumann, Mueller & Larson, P.C.

(57) ABSTRACT

Flaky particles of the present invention have a particle size distribution in which a value of D90/D10 is at least 2.0 but not more than 3.0, a value of D10 is at least 4.7 μm but not more than 25 μm, and a maximum particle diameter is 90 μm or less, where D10 is defined as a particle diameter at which a cumulative volume of particles reaches 10% when counted from the smaller side, and D90 is defined as a particle diameter at which a cumulative volume of particles reaches 90% when counted from the smaller side. A luster pigment of the present invention contains flaky particles and at least one selected from a metallic layer and a metallic oxide layer that are formed on at least a part of the surface of each of the flaky particles. The luster pigment has a particle size distribution in which a value of D90/D10 is at least 2.0 but not more than 3.0, a value of D10 is at least 4.7 μm but not more than 25 μm, and a maximum particle diameter is 90 μm or less, where D10 is defined as a particle diameter at which a cumulative volume of particles reaches 10% when counted from the smaller side, and D90 is defined as a particle diameter at which a cumulative volume of particles reaches 90% when counted from the smaller side.

11 Claims, 1 Drawing Sheet

(56) References Cited

U.S. PATENT DOCUMENTS

| | | | |
|---|---|---|---|
| 2006/0068116 A1* | 3/2006 | Chilla et al. | 427/402 |
| 2006/0137488 A1 | 6/2006 | Sakaue et al. | |
| 2006/0223910 A1* | 10/2006 | Bagala, Sr. | 523/200 |

FOREIGN PATENT DOCUMENTS

| | | |
|---|---|---|
| JP | 4-002636 A | 1/1992 |
| JP | 9-141194 A | 6/1997 |
| JP | 11-152423 A | 6/1999 |
| JP | 2000-090930 | 3/2000 |
| JP | 2000-273349 A | 10/2000 |
| JP | 2000-273350 A | 10/2000 |
| JP | 2001-011340 A | 1/2001 |
| JP | 2001-031421 A | 2/2001 |
| JP | 2002-155240 A | 5/2002 |
| JP | 2004-169155 | 6/2004 |
| JP | 2005-200734 | 7/2005 |

OTHER PUBLICATIONS

Kurata, Yutaka, "Saishin Funtai Bussei Zusetsu" (Physical Properties of Powder Particles with Illustrations, Latest Version), Third edition, NGT Co., Jun. 30, 2004.

Japanese Office Action with its English translation dated Jun. 29, 2010 corresponding to Japanese Patent Application No. 2008-508700, 6 pages.

Anonymous, "Aluminum Paste STAPA IL Hydrolan 2154 No. 55900/G" ECKART Effect Pigments Technical Data Sheet, URL:http://productdatabase.altana-ep-staging.de/datasheets/technical/en/ee-05477.pdf—1 page.

* cited by examiner

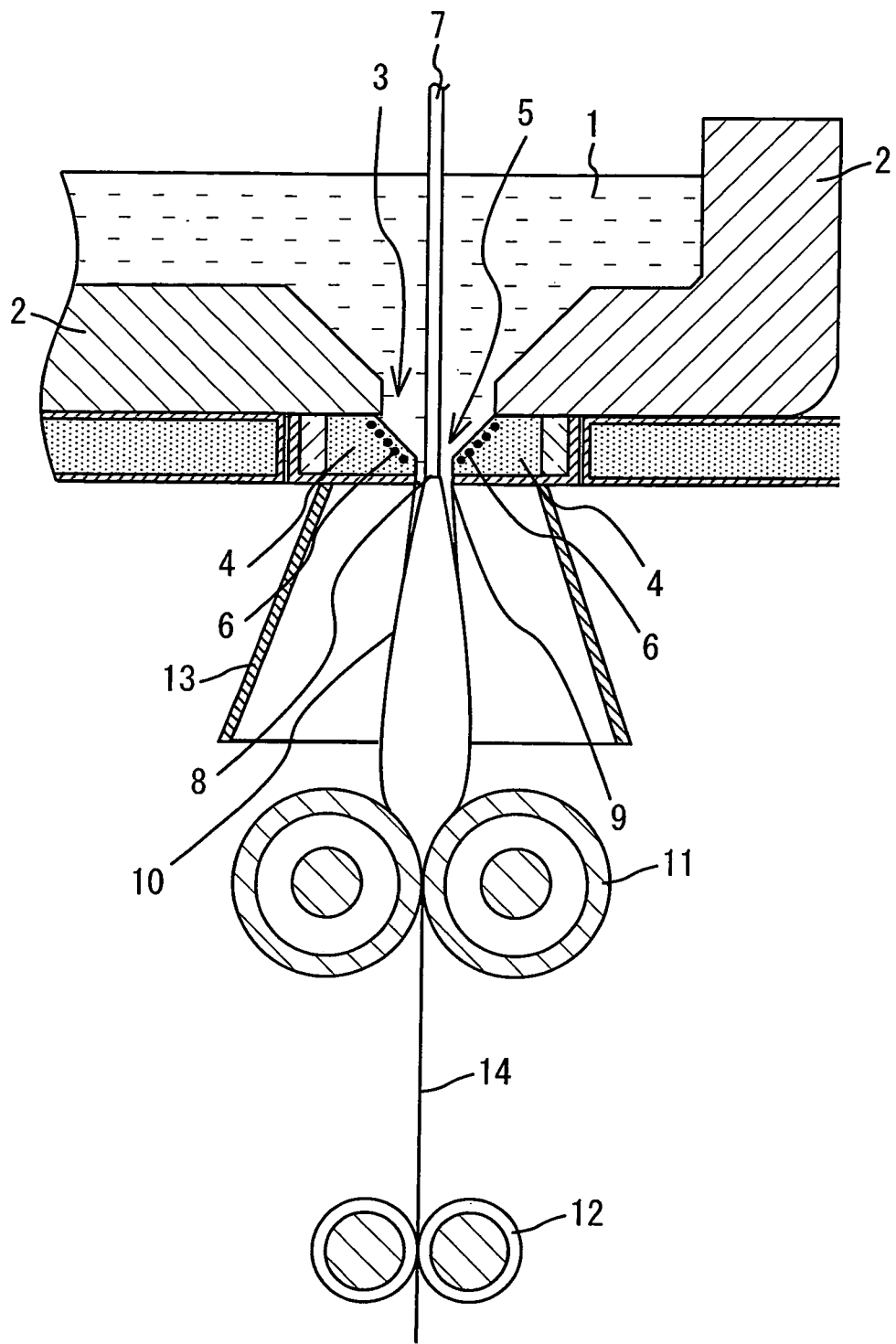

FLAKY PARTICLES AND LUSTER PIGMENT, AND COSMETIC, COATING COMPOSITION, RESIN COMPOSITION AND INK COMPOSITION EACH CONTAINING THE SAME

TECHNICAL FIELD

The present invention relates to flaky particles and a luster pigment, and a cosmetic, a coating composition, a resin composition and an ink composition, each containing at least one of the flaky particles and the luster pigment.

BACKGROUND ART

Conventionally, as a luster pigment exhibiting pearl luster (hereinafter referred also to as a pearl luster pigment), there have been flaky particles, such as mica, synthetic mica, talc, flaky glass, flaky silica and flaky bismuth oxychloride, each coated with a metallic oxide such as a titanium oxide and an iron oxide. Flaky particles coated with two or more layers of these metallic oxides also have been proposed (see, for example, "Ganryo no Jiten" (Dictionary of Pigments), First edition, edited by Seiji ITO, published by Asakura Publishing Co., Ltd, Sep. 25, 2000, pp 239-241).

As a luster pigment exhibiting metallic luster (hereinafter referred also to as a metallic luster pigment), there have been flaky particles, such as flaky glass, mica and synthetic mica, each coated with a metal such as silver, gold and nickel (see, for example, JP 62 (1987)-175045 Y and JP 04 (1992)-2636 A).

Metallic luster pigments are not limited only to the flaky particles coated with metals or metallic oxides as described above. Some of the metallic luster pigments are made from flaky particles themselves made of metals such as aluminum and copper with no coating on their surfaces (see, for example, "Ganryo no Jiten" (Dictionary of Pigments), First edition, edited by Seiji ITO, published by Asakura Publishing Co., Ltd, Sep. 25, 2000, pp 232-234). Fish scale foil and flaky bismuth oxychloride themselves are sometimes used as pearl luster pigments (see, for example, "Ganryo no Jiten" (Dictionary of Pigments), First edition, edited by Seijiro ITO, published by Asakura Publishing Co., Ltd, Sep. 25, 2000, pp 239-241).

The luster pigments employing the flaky particles as described above (hereinafter, these luster pigments simply may be referred to as pigments) reflect light on their smooth surfaces and thus exhibit a satisfactory lustrous appearance.

Furthermore, a lustrous coating composition has been proposed in which the particle size of a luster pigment is adjusted so as to obtain a lustrous appearance and to prevent a filter from clogging during circulation for coating (see, for example, JP 2002-155240 A).

However, flaky particles used for conventional luster pigments each have a wide range of particle size distribution and have a high content of fine particles and coarse particles. Therefore, not only pigments made from flaky particles themselves but also pigments made from flaky particles coated with metallic layers and/or metallic oxide layers each have a wide range of particle size distribution.

Assume, for example, a case where a pearl luster pigment is produced by using flaky particles with a wide range of particle size distribution (that is, having a high content of fine particles and coarse particles) as a substrate and coating the substrate with a high refractive material such as titanium oxide. A high content of fine particles in the pigment causes a problem such as a decrease in lustrous appearance or a smooth and flat appearance without any particulate appearance. On the other hand, a high content of coarse particles in the pigment causes other problems. For example, a filter clogs when a coating composition containing this pearl luster pigment is filtered, the pigment particles are not oriented regularly in a coating film obtained by applying the coating composition and thereby a part of the pigment particles protrude through the film, and excessively large particles of the pigment are detectable as foreign substances in the coating.

Furthermore, even if the particle size of a luster pigment is adjusted as proposed in JP 2002-155240 A, it is difficult to realize a luster pigment capable of solving these problems completely. That is, it is difficult to realize a luster pigment having a good balance between desirable properties of achieving satisfactory lustrous appearance and particulate appearance and of inhibiting more reliably filter clogging and detection of foreign substances.

DISCLOSURE OF INVENTION

Under these circumstances, it is an object of the present invention to provide flaky particles capable of achieving highly lustrous appearance and particulate appearance and of inhibiting the occurrence of problems such as filter clogging and detection of foreign substances when they are used for pigments. It is another object of the present invention to provide a luster pigment capable of achieving highly lustrous appearance and particulate appearance and of inhibiting the occurrence of problems such as filter clogging and detection of foreign substances. It is still another object of the present invention to provide a cosmetic, a coating composition, a resin composition and an ink composition, each containing the flaky particles and/or the luster pigment.

The flaky particles of the present invention have a particle size distribution in which a value of D90/D10 is at least 2.0 but not more than 3.0, a value of D10 is at least 4.7 µm but not more than 25 g/m, and a maximum particle diameter is 90 µm or less, where D10 is defined as a particle diameter at which a cumulative volume of particles reaches 10% when counted from the smaller side, and D90 is defined as a particle diameter at which a cumulative volume of particles reaches 90% when counted from the smaller side.

It should be noted that in the present description, flaky particles are, for example, scaly particles having a thickness in a range of 0.1 to 8.0 µm and an aspect ratio (average particle diameter/average thickness) of approximately 2 to 100. The particle diameter of a flaky particle is a light scattering equivalent diameter obtained when the flaky particle is measured by a laser diffraction/scattering method. According to "Saishin Funtai Bussei Zusetsu (Physical Properties of Powder Particles with Illustrations, Latest Version), Third edition" (issued by Yutaka KURATA, published by NGT Co., Jun. 30, 2004), for example, a light scattering equivalent diameter is defined as a diameter of a sphere that exhibits a light scattering pattern closest to a light scattering pattern of a particle obtained by a measurement and that has the same refractive index as that of the particle.

A particle size distribution is an index indicating the size (diameters) of particles to be measured and the relative amounts of the particles sorted according to the size. In the present description, the particle size distribution is measured based on a laser diffraction/scattering method. The laser diffraction/scattering method is a method for obtaining a particle size distribution by employing light scattered when particles are irradiated with light. In the particle size distribution in the present description, a volume is used as a measure of an amount of particles. The definitions of D10 and D90 are as described above. D50 (a particle diameter at which the cumulative volume of particles reaches 50% in a particle size distribution) indicates an average particle diameter. D90/D10 can be an index indicating a range of particle size distribution. When average particle diameters (D50 values) are almost equal, particles with a larger value of D90/D10 have a wider range of particle size distribution, and particles with a smaller value of D90/D10 has a narrower range of particle size distribution (a content of fine particles and coarse particles is lower). A maximum particle diameter is a particle diameter at which the cumulative volume of particles reaches 100% in the particle size distribution.

The flaky particles of the present invention have a value of D90/D10 of at least 2.0 but not more than 3.0, a value of D10 of at least 4.7 μm but not more than 25 μm, and a maximum particle diameter of 90 μm or less. The range of particle size distribution of the flaky particles is narrow. That is, the flaky particles have a low content of fine particles and coarse particles. The lower content of fine particles and the D10 value of 4.7 μm or more make it possible to achieve highly lustrous appearance and particulate appearance when they are used for a pigment, for example. The lower content of coarse particles and the maximum particle diameter of 90 μm or less make it possible to inhibit the occurrence of problems such as filter clogging and detection of the particles as foreign substances when they are used for a pigment for coatings, for example. Furthermore, since the D10 value of 25 μm or less means that coarse particles do not dominate the distribution, a not excessively but moderately lustrous appearance can be obtained.

The luster pigment of the present invention contains flaky particles and at least one selected from a metallic layer and a metallic oxide layer that are formed on at least a part of the surface of each of the flaky particles. The luster pigment has a particle size distribution in which a value of D90/D10 is at least 2.0 but not more than 3.0, a value of D10 is at least 4.7 μm but not more than 25 μm, and a maximum particle diameter is 90 μm or less, where D10 is defined as a particle diameter at which a cumulative volume of particles reaches 10% when counted from the smaller side, and D90 is defined as a particle diameter at which a cumulative volume of particles reaches 90% when counted from the smaller side. The particle size distribution of the luster pigment of the present invention is measured on the same principle as in the particle size distribution of the flaky particles of the present invention. The index indicated by D10/D90 also is as described above. In addition, the definitions of the flaky particles, the particle diameters of the flaky particles and the maximum particle diameter to be used for the luster pigment of the present invention are the same as those of the flaky particles of the present invention.

The luster pigment of the present invention has a value of D90/D10 of at least 2.0 but not more than 3.0, a value of D10 of at least 4.7 μm but not more than 25 μm, and a maximum particle diameter of 90 μm or less. The range of particle size distribution of the luster pigment is narrow. That is, the luster pigment has a low content of fine particles and coarse particles. The lower content of fine particles and the D10 value of 4.7 μm or more make it possible to achieve highly lustrous appearance and particulate appearance. The lower content of coarse particles and the maximum particle diameter of 90 μm or less make it possible to inhibit the occurrence of problems such as filter clogging and detection of foreign substances when the luster pigment is used as a pigment for coatings, for example. Furthermore, since the D10 value of 25 μm or less means that coarse particles do not dominate the distribution, a not excessively but moderately lustrous appearance can be obtained.

The cosmetic of the present invention contains at least one selected from the flaky particles of the present invention and the luster pigment of the present invention.

The coating composition of the present invention contains at least one selected from the flaky particles of the present invention and the luster pigment of the present invention.

The resin composition of the present invention contains at least one selected from the flaky particles of the present invention and the luster pigment of the present invention.

The ink composition of the present invention contains at least one selected from the flaky particles of the present invention and the luster pigment of the present invention.

The cosmetic, coating composition, resin composition and ink composition of the present invention each contain at least one selected from the flaky particles of the present invention and the luster pigment of the present invention. Therefore, it is possible to achieve a highly lustrous appearance and particulate appearance, and to inhibit problems such as filter clogging when filtering the particles and protrusion of foreign substances.

BRIEF DESCRIPTION OF DRAWINGS

FIG. 1 is a partial cross-sectional view schematically showing an example of an apparatus for manufacturing glass flakes as flaky particles of the present invention.

BEST MODE FOR CARRYING OUT THE INVENTION

Hereinafter, embodiments of the present invention will be described.

First Embodiment

In the first embodiment, the flaky particles of the present invention are described.

The flaky particles of the present embodiment have a particle size distribution in which a value of D90/D10 of at least 2.0 but not more than 3.0, a value of D10 of at least 4.7 μm but not more than 25 μm, and a maximum particle diameter of 90 μm or less. Thus, when the range of particle size distribution of the flaky particles is narrowed so that the value of D10 and the maximum particle diameter are limited within the above-mentioned ranges, it is possible to obtain a highly lustrous appearance and particulate appearance when the flaky particles are used for a pigment, for example, and to prevent problems such as detection of foreign substances and filter clogging when they are used for cosmetics, coatings, and the like. Therefore, in order to make the range of particle size distribution narrower, the value of D90/D10 may be in a range of at least 2.4 but not more than 2.9, for example. The lower limit of the maximum particle diameter is not particularly limited, but it may be 75 μm, for example, and preferably is 45 μm.

The flaky particles of the present embodiment themselves can be used as a pearl luster pigment or a metallic luster pigment, or as a substrate for a luster pigment such as a pearl luster pigment and a metallic luster pigment. When the flaky particles are used as a substrate for a luster pigment, a metallic layer or a metallic oxide layer should be formed on at least a part of the surface of each of the flaky particles. Preferably, the entire surface of the substrate is coated with a metallic layer or a metallic oxide layer. When the flaky particles of the present embodiment are used as, for example, a substrate for a luster pigment, examples of the flaky particles include mica, synthetic mica, talc, flaky glass, flaky silica, and flaky bismuth oxychloride. When the flaky particles of the present embodiment are used by themselves as a luster pigment, examples of the flaky particles that can be used include flakes made of a metal such as aluminum and copper (hereinafter referred to also as metallic flakes), fish scale foil, and flaky bismuth oxychloride.

The average particle diameter (D50) of the flaky particles of the present embodiment may be, for example, at least 7 μm but not more than 80 μm. The flaky particles with an average particle diameter of this range are used suitably as a pigment for cosmetics and coatings, for example.

Next, a method of producing flaky particles having a particle size distribution in which the value of D90/D10 is at least 2.0 but not more than 3.0, the value of D10 is at least 4.7 μm but not more than 25 μm, and the maximum particle diameter is 90 μm or less is described below.

In the present embodiment, the particle size of flaky particles is adjusted by, for example, classification, so as to achieve the particle size distribution as described above. A case of using sieve classification is described here. For example, a dry-type vibrating sieving machine can be used for sieve classification. First, coarse particles are removed using a sieve with a mesh of a predetermined size or larger (with a coarse mesh), and then fine particles are removed using a sieve with a mesh of a predetermined size or smaller (with a fine mesh). Thus, the flaky particles having the particle size distribution of the present embodiment can be obtained. In this case, if ultrasonic oscillation is used together, the fine particle removing effect can further be enhanced. It should be noted that the mesh opening of a sieve to be used here may be selected appropriately depending on the particle size of unsieved particles, the average particle diameter and D90/D10 value (desired range of particle size distribution) of particles to be obtained, and others. The removed coarse particles can be reused by repulverization and reclassification thereof. The removed fine particles can be used for other products and the like.

A method of producing flaky particles of the present embodiment is described below by taking glass flakes as an example. First, glass flakes are produced using a blowing method as disclosed in JP 45 (1970)-3541 B and a method as disclosed in JP 41 (1966)-17148 B. A method of producing glass flakes using the blowing method is described here. The blowing method is a method in which a molten glass base material which is continuously taken out from a molten glass source is stretched while being inflated into a hollow shape so as to obtain a thin glass film. By crushing the glass film obtained by this method, the glass flake filler of the present embodiment can be produced.

FIG. 1 shows an example of an apparatus for manufacturing a glass film by the blowing method. In FIG. 1, 1 is a molten glass base material, 2 is a fire-resistant furnace tank, and 3 is a hole provided on the bottom of the furnace tank. 4 is a feeder block having a small circular glass outlet opening 5 that is smaller than the hole 3. The feeder block 4 is made of refractory cast brick in which electric heating wires 6 are embedded. The temperature of the molten glass base material at the glass outlet opening 5 is maintained constant by the electric heating wires 6. 7 is a blow nozzle disposed from above the fire-resistant furnace tank 2 to the glass outlet opening 5 through the hole 3. The tip 8 of the blow nozzle 7 forms a circular slit 9 in the glass outlet opening. The molten glass base material flowing from the slit 9 is inflated with gas (for example, air) blown through the blow nozzle 7, so as to form a hollow shape. Then, the hollow glass further is stretched downward, thereby making the thickness of the resulting film very thin. 11 is a pair of pressure rolls, and 12 is a pair of stretching rolls. 13 is a diverging cylindrical steel reflecting plate. The hollow glass 10 is not only blocked from outside airflow but also kept hot enough by the reflecting plate 13, which results in a uniformly-inflated thin hollow glass. The hollow glass 10 thus inflated is pressed flat by the pressure rolls 11, and the resulting flat glass film 14 is discharged. The glass film thus obtained is crushed with a roll, for example. Thus, glass flakes can be obtained. It should be noted that glass flakes with a desired thickness can be produced by adjusting appropriately the speed of stretching the hollow glass and the pressure of gas fed through the blow nozzle during the production of the glass flakes using the above apparatus.

By classifying the glass flakes thus produced by considering a desired average particle diameter and particle size distribution, glass flakes as the flaky particles of the present embodiment can be obtained.

In the present embodiment, sieve classification is used as a classification method, but other classification methods may be used to remove fine particles and coarse particles.

In the case of dry classification, an airflow classifier such as a gravitational classifier, an inertial classifier, and a centrifugal classifier can be used. As a gravitational classifier, horizontal flow type, vertical flow type, and inclined flow type classifiers, for example, can be used. As an inertial classifier, linear type, curving type, and louver type classifiers, and an Elbow-Jet, and a Variable Impactor, for example, can be used. As a centrifugal classifier making use of air vortex, cyclone type, Vantongeren type, and classiclone type classifiers, a Dispersion Separator, and a Microplex can be used. As a centrifugal classifier making use of mechanical rotation, a Micron Separator, a Turboplex, an Acucut, a Turbo Classifier, and the like can be used.

In the case of wet classification, an airflow classifier such as a gravitational classifier and a centrifugal classifier can be used. As a gravitational classifier making use of gravity settling tanks, a settling tank, a deposition cone, a Spitzkasten and a Hydroseparator can be used. As a gravitational classifier making use of mechanical rotation, a drag chain classifier, a rake classifier, a ball classifier, a spiral classifier and the like can be used. As a hydraulic classifier, a "doruko" sizer, a Valenwald sizer, a syphon sizer, a hydroscillator, and the like can be used. As a centrifugal classifier, hydrocyclone and centrifugal classifiers (disk type and decanter type) and the like can be used.

Second Embodiment

In the second embodiment, the luster pigment of the present invention is described.

In the luster pigment of the present embodiment, at least one selected from a metallic layer and a metallic oxide layer is formed on at least a part of the surface of each of the flaky particles serving as a substrate. It is preferable that the entire surface of the flaky particle is coated with the metallic layer or metallic oxide layer. The luster pigment of the present embodiment has a particle size distribution in which a value of D90/D10 is at least 2.0 but not more than 3.0, a value of D10 is at least 4.7 μm but not more than 25 μm, and a maximum particle diameter of 90 μm or less. The range of particle size distribution of the luster pigment is thus narrowed, and further the value of D10 and the maximum particle diameter are limited within the above ranges. As a result, when this luster pigment is used as a filler for cosmetics and coatings, a product having highly lustrous appearance and particulate appearance can be obtained, and problems such as detection of foreign substances and filter clogging also can be inhibited. Therefore, in order to make the range of particle size distribution narrower, the value of D90/D10 may be in a range of at least 2.4 but not more than 2.9. The lower limit of the maximum particle diameter is not particularly limited, but it may be 75 μm, for example, and preferably is 45 μm.

Examples of flaky particles that can be used for the luster pigment of the present embodiment include mica, synthetic mica, talc, flaky glass, flaky silica, and flaky bismuth oxychloride. It is preferable to use, among these flaky particles, flaky glass as a substrate for a luster pigment because the flaky glass can achieve a higher transparency than other materials and this high transparency is more emphasized when a luster pigment, like the luster pigment of the present embodiment, has a low content of fine particles.

In addition, in the luster pigment of the present embodiment, it is preferable to use, as a substrate, the flaky particles as described in the first embodiment in order to adjust the particle size distribution of the luster pigment more easily.

The metallic layer to be used for the pigment of the present embodiment can be formed of a metal such as silver, gold and nickel. Metallic luster pigments can be obtained by coating flaky particles with these metallic layers. The metallic oxide layer can be formed of a metallic oxide such as titanium oxide and iron oxide. Pearl luster pigments can be obtained by coating flaky particles with these metallic oxide layers.

The average particle diameter (D50) of the luster pigment of the present embodiment may be, for example, at least 7 μm but not more than 80 μm. The flaky particles with an average particle diameter of this range are used suitably as a pigment for cosmetics and coatings, for example.

Any known method may be used as a method for coating flaky particles with a metallic layer or the like. For example, a method as disclosed in JP 2001-031421 A and JP 2001-11340 A can be used. Specifically, this is a method in which, in order to coat flaky particles with a titanium oxide layer, for example, the flaky particles are suspended in an aqueous solution of titanyl sulfate or titanium tetrachloride, and the resulting slurry is increased in temperature so as to precipitate titania, and thus a coating film is formed on the surface of each flaky particle. The method for coating flaky particles is not limited to this method. Any method can be used as long as a thin coating film can be formed on the surface of each flaky particle. The thickness of a metallic layer or a metallic oxide layer is not particularly limited. In view of the achievement of the lustrous appearance and the cost, when the particles are coated with a metal, the thickness of the coating film is preferably 0.04 to 2 μm, for example. When the particles are coated with a metallic oxide, the thickness of the coating film is preferably 0.01 to 1 μm, for example.

As a method of producing a luster pigment having a particle size distribution in which the value of D90/D10 is at least 2.0 but not more than 3.0, the value of D10 is at least 4.7 μm but not more than 25 μm, and the maximum particle diameter is 90 μm or less, a method of adjusting the particle size distribution of flaky particles (classification method) as described in the first embodiment can be used. That is, by classifying the size of flaky particles coated with a metallic layer or the like, a luster pigment having a particle size distribution like that of the luster pigment of the present embodiment can be produced.

Third Embodiment

In the present embodiment, a cosmetic, a coating composition, a resin composition and an ink composition, each containing at least one selected from the flaky particles described in the first embodiment and the luster pigment described in the second embodiment, are described. The cosmetic, the coating composition, the resin composition and the ink composition as described below each may contain only one of the flaky particles and the luster pigment, or may contain both of them.

The cosmetic of the present embodiment contains at least one (hereinafter also referred to as a filler) selected from the flaky particles of the first embodiment (particles that can be used by themselves as a pigment) and the luster pigment of the second embodiment. Thus, the cosmetic can develop more lustrous colors than ever before, and also feels good to the touch. The content of the filler in the cosmetic (the total content of the flaky particles and the luster pigment when both of them are contained, and this will apply likewise hereinafter) is not particularly limited, and is selected appropriately depending on the products to be obtained. In addition to the filler, other components that are contained in commonly available cosmetics can be blended appropriately in the cosmetic as required.

Since the coating composition of the present embodiment contains the filler as in the cosmetic, it can present a more lustrous appearance than ever before. Although the content of the filler in the coating composition is not particularly limited, it can be, for example, 0.05 to 30% by mass in view of an adequate lustrous appearance of the coating film. In addition to the filler, other components that are contained in commonly available coating compositions can be blended appropriately in the coating composition as required.

Since the resin composition of the present embodiment contains the filler as in the cosmetic, it can present a more lustrous appearance than ever before. Although the content of the filler in the resin composition is not particularly limited, it can be, for example, 0.05 to 30% by mass in view of an adequate lustrous appearance of the resin composition and effects to be imposed on the physical properties of the resin composition. In addition to the filler, other components that are contained in commonly available resin compositions can be blended appropriately in the resin composition as required. The resin to be used here is not particularly limited. Examples of the resin include thermoplastic resins such as polyolefin resins like polyethylene and polypropylene, polyvinyl chloride resin, polystyrene resin, acryl resin, methacryl resin, ABS resin, AES resin, AS resin, polyamide, polycarbonate resin, polybutylene terephthalate resin, polyethylene terephthalate resin, polyacetal resin, polyphenylene ether resin, polysulfone resin, and fluororesin. Copolymers, mixtures, and modified substances of these polymers also can be used.

Since the ink composition of the present embodiment contains the filler as in the cosmetic, it can present a more lustrous appearance than ever before. Although the content of the filler in the ink composition is not particularly limited, it can be, for example, 0.05 to 30% by mass in view of an adequate lustrous appearance. In addition to the filler, other components that are contained in commonly available ink compositions can be blended appropriately in the ink composition as required. Examples of the ink composition include inks for writing instruments such as ball-point pens, gel ink pens and poster paint pens, and printing inks such as gravure printing ink, letterpress printing ink, intaglio printing ink and screen printing ink.

EXAMPLES

Hereafter, the present invention is described in further detail with reference to Examples. The following Examples each show the case where glass flakes were used as the flaky particles. The present invention is not limited to this case. As the flaky particles, mica, synthetic mica, flaky bismuth oxychloride, and the like may be used.

In Examples and Comparative Examples described below, pulverization for producing glass flakes, classification for adjusting particle size distribution, measurement of particle size distribution, evaluation of lustrous appearance and particulate appearance, evaluation of filter clogging, and evaluation of detection of foreign substances in coatings were carried out by the following methods.

<Pulverization>

Glass flakes were pulverized using a jet mill type pulverizer (Product name "Labojet LJ" manufactured by Nippon Pneumatic Mfg. Co., Ltd.).

<Classification>

Particle size was adjusted by sieve classification.

As a vibrating sieving machine, an electromagnetic sieve shaker (Product name "RETSCH SIEVE SHAKER, type VIBRO" manufactured by RETSCH Co., Ltd.) was used. Standard sieves, each having a diameter of +200 mm and a height of 45 mm, were used. As standard sieves, sieves with mesh openings of 16, 20, 25, 32, 38, and 45 µm respectively (manufactured by Iida Seisakusho, Co., Ltd.) were prepared. A suitable sieve was selected for each particle size distribution to be obtained, as required.

Sieving was carried out in the following manner. A sieve with a predetermined coarse mesh opening, a sieve with a predetermined fine mesh opening, and a receiving pan were stacked in this order from the top, and set up in an electromagnetic sieve shaker. Then, sieving was carried out for a predetermined time period. Coarse particles are removed by the upper sieve, and glass flakes containing little coarse particles drop into the middle sieve. Fine particles are removed by the middle sieve, and the fine particles drop below the sieve. As a result, glass flakes from which both coarse particles and fine particles are removed remain in the middle sieve. These are the glass flakes serving as the flaky particles of the present invention with a narrow range of particle size distribution. The particle size of unsieved glass flakes, mesh openings of the sieves, sieving power, and sieving time were adjusted appropriately, so that the obtained glass flakes had various particle size distributions.

<Measurement Method of Particle Size Distribution>

The particle size distribution was measured using a laser diffraction particle size distribution analyzer (Product name "Microtrack HRA" manufactured by Nikkiso Co., Ltd.). An average particle diameter D50, a maximum particle diameter, a D90 value and a D10 value were read out from the measurement results, and further D90/D10 value was calculated to determine whether the range of the particle size distribution was wide or narrow.

<Evaluation of Transparency>

The following two types of coatings were prepared: an acrylic resin coating (without flaky particles) (Product name "Acryl Auto Clear Super" manufactured by NIPPON PAINT Co., Ltd.) (including a solid content of about 50% by mass) alone; and a mixture (with flaky particles) obtained by adding sample flaky particles in this acrylic resin coating so that the content of the flaky particles was 10% by mass in the resin and mixing and stirring well. These two types of coatings were applied to a hiding power test paper using an applicator with a gap of 9 mils (9/1000 inches) so that two lines of coatings were provided in parallel, and dried. The hues (L values) of the black area of the coated paper were measured using a colorimeter (CR-300 manufactured by Minolta Co., Ltd.). Thus, the difference of the L values (ΔL) resulted from whether or not the flaky particles were contained was obtained. It was evaluated that a smaller ΔL value indicated a higher transparency.

<Evaluation of Lustrous Appearance and Particulate Appearance>

Sample flaky particles were added in an acrylic resin coating (Product name "Acryl Auto Clear Super" manufactured by NIPPON PAINT Co., Ltd.) (including a solid content of about 50% by mass) so that the content of the flaky particles was 10% by mass in the resin, and mixed and stirred well. After that, each coating thus prepared was applied to a hiding power test paper using an applicator with a gap of 9 mils (9/1000 inches), and dried. The hue (L value) of the coated paper was measured using a colorimeter (CR-300 manufactured by Minolta Co., Ltd.). It was evaluated that a coating having a higher L value that is a measure of lightness had a more lustrous appearance.

Furthermore, the above-mentioned coated paper for luminance measurement also were prepared and observed visually so as to evaluate the particulate appearance and lustrous appearance. The evaluation standards are shown below.

(Evaluation Standards (Visual Observation of Coated Paper))

The particulate appearance and lustrous appearance were evaluated on the following five-point scale.

5: Very highly particulate and lustrous appearance - - - Each particle of a pigment can be observed and exhibits a lustrous appearance strongly.

4: Highly particulate appearance - - - Each particle of a pigment can be observed and exhibits a lustrous appearance.

3: Moderately particulate appearance - - - Each particle of a pigment can be observed but does not exhibit a lustrous appearance so strongly.

2: Less particulate appearance - - - Each particle of a pigment can be found if it is seen carefully, but is poorly visible and has a flat and smooth appearance.

1: No particulate appearance - - - No particulate appearance is seen at all, and an overall impression is like a wall, which is slightly lustrous.

<Evaluation of Filter Clogging>

An appropriate amount of thinner was added to 78 mass % of acrylic resin (Product name "Acrydec A-322" manufactured by Dainippon Ink & Chemicals, Inc.), 16 mass % of butylated melamine resin (Product name "Super Beckamine L-117-60" manufactured by Dainippon Ink & Chemicals, Inc.), and 6 mass % of each sample pigment, and mixed well using a blender so that the viscosity of the mixture was 13 seconds (as measured at 20° C. with a Ford cup No. 4 manufactured by Yasuda Seiki Seisakusho Ltd.). Thus, each lustrous coating was prepared. This lustrous coating was filtered through a triangle filter (made of nylon, with a No. 200 mesh (with a mesh opening of about 75 µm)), and the degree of clogging of the filter was observed visually.

(Evaluation Standards (Visual Observation of Filter Clogging))

The degree of filter clogging was evaluated on the following three-point scale.

3: No clogging is seen
2: Clogging is seen slightly
1: Obvious and significant clogging is seen <Evaluation of Detection of Foreign Substances in Coating>

An appropriate amount of thinner was added to 78 mass % of acrylic resin (Product name "Acrydec A-322" manufactured by Dainippon Ink & Chemicals, Inc.), 16 mass % of butylated melamine resin (Product name "Super Beckamine L-117-60" manufactured by Dainippon Ink & Chemicals, Inc.), and 6 mass % of each sample pigment, and mixed well using a blender so that the viscosity of the mixture was 13 seconds (as measured at 20° C. with a Ford cup No. 4 manufactured by Yasuda Seiki Seisakusho Ltd.). Thus, each lustrous coating serving as a base coating was prepared. This lustrous coating was applied to a dull steel plate (of 0.8 mm in thickness×100 mm in width×500 mm in length) using a spray gun (W-100 manufactured by Anest Iwata Corporation), and then baked (at 130° C. for 10 minutes). Thus, each base layer with a thickness of 15 μm was formed.

Next, thinner was added to 72 mass % of acrylic resin (Product name "Acrydec A-345" manufactured by Dainippon Ink & Chemicals, Inc.), and 28 mass % of butylated melamine resin (Product name "Super Beckamine L-117-60" manufactured by Dainippon Ink & Chemicals, Inc.), and mixed well using a blender so that the viscosity of the mixture was 24 seconds (as measured at 20° C. with a Ford cup No. 4 manufactured by Yasuda Seiki Seisakusho Ltd.). Thus, each top clear coating composition was prepared. This top clear coating composition was applied to the dull steel plate on which the base layer was formed, using a spray gun (W-100 manufactured by Anest Iwata Corporation), and then baked (at 140° C. for 30 minutes). Thus, each top clear layer with a thickness of 30 μm was formed.

(Evaluation Standards (Visual Observation of Occurrence Frequency of Foreign Substances in Coating))

The surface of the dull steel plate (of 0.8 mm in thickness× 10 mm in width×500 mm in length) covered with the coating was observed visually, and the coating was evaluated by calculating the number of particles that can be detected as foreign substances.

Examples 1 to 3

Glass flakes as a substrate were produced using an apparatus shown in FIG. 1. Glass is melted at 1200° C., stretched while being blown up into a hollow shape to form a thin film, and further cooled to be solidified. The thin film was crushed with a roll, and thus glass flakes with a thickness of 1.3 μm were obtained. The glass flakes thus obtained were pulverized using a jet mill type pulverizer so that the glass flakes had an average particle diameter of about 20 μm. Thus, the glass flakes having an average particle diameter D50 of 21.7 μm were produced. As for these glass flakes, the maximum particle diameter was 96.0 μm, D90 value was 37.2 μm, D10 value was 10.8 μm and D90/D10 value was 3.44.

These glass flakes were sieved for a predetermined time period using a standard sieve with a mesh opening of 32 μm, a sieve with a mesh opening of 20 μm, and a receiving pan that are stacked in this order from the top, so that coarse particles and fine particles were removed. The particle size distribution of the glass flakes collected on the middle sieve was measured. Glass flakes having various particle size distributions were obtained by changing sieving time. Table 1 shows the measurement results thereof. In Table 1, "original flakes" mean original (unsieved) glass flakes. The same goes for other Tables below.

TABLE 1

|  | Original flakes | Example 1 | Example 2 | Example 3 |
|---|---|---|---|---|
| Sieving time (minutes) | — | 30 | 45 | 60 |
| Average particle diameter D50 (μm) | 21.7 | 24.4 | 22.5 | 21.0 |
| Maximum particle diameter (μm) | 96.0 | 74.0 | 80.7 | 88.0 |
| D90 (μm) | 37.2 | 38.8 | 36.3 | 34.5 |
| D10 (μm) | 10.8 | 15.5 | 13.4 | 11.7 |

TABLE 1-continued

|  | Original flakes | Example 1 | Example 2 | Example 3 |
|---|---|---|---|---|
| D90/D10 | 3.44 | 2.50 | 2.71 | 2.95 |
| Without flaky particles L value of black area | 20.8 | 20.8 | 20.8 | 20.8 |
| With flaky particles L value of black area | 24.1 | 22.0 | 22.7 | 23.3 |
| ΔL | 3.3 | 1.2 | 1.9 | 2.5 |

Table 1 shows that in Examples 1, 2 and 3, the D90/D10 values were 2.50, 2.71 and 2.95 respectively, whereas the D90/D10 value of the original glass flakes was 3.44, and thus it was confirmed that glass flakes with narrow ranges of particle size distributions were obtained. Table 1 also shows that the maximum diameters of Examples 1, 2 and 3 were 74.0 μm, 80.7 μm and 88.0 μm respectively, whereas the maximum diameter of the original flakes was 96.0 μm. The D10 values of Examples 1, 2 and 3 were 15.5 μm, 13.4 μm and 11.7 μm respectively, whereas the D10 value of the original flakes was 10.8 μm. The ΔL values of Examples 1, 2 and 3 were 1.2, 1.9 and 2.5 respectively, whereas the ΔL value of the original flakes was 3.3. As described above, it is found that coarse particles and fine particles can be removed effectively by the above-mentioned method, thereby enhancing transparency.

Examples 4 to 6, and Comparative Examples 1 and 2

Classified glass flakes of Examples 1 to 3 were coated with titanium oxide. Ion exchanged water was added to 50 g of the glass flakes so that the total amount thereof was 0.5 liter, and then the resulting aqueous solution was adjusted to pH 1.0 with hydrochloric acid of 35% by mass and heated to 75° C. An aqueous titanium tetrachloride solution (containing titanium of 16.5% by mass) was added quantitatively at the rate of 12 g per hour, and an aqueous caustic soda solution (containing caustic soda of 10% by mass) was also added at the rate of 60 milliliters per hour, while being stirred continuously, until a lustrous product with a silver pearl tone was obtained.

When the product with the target color tone was obtained, the product was collected by filtration under reduced pressure, washed with pure water, dried at 150° C., and baked at 600° C. Thus, glass flakes each coated with a titanium oxide film were obtained as a pearl luster pigment. Pearl luster pigments (luster pigments) of Examples 4, 5 and 6 were produced using the glass flakes of Examples 1, 2 and 3. Table 2 shows the evaluation results of these pearl luster pigments.

As Comparative Examples, two lots of METASHINE (registered trademark) MC 1020 RS (manufactured by Nippon Sheet Glass Co., Ltd.) were prepared and the particle size distributions (average particle diameters, maximum particle diameters, D90 values, D10 values and D90/D10 values) and L values thereof were measured. METASHINE (registered trademark) MC 1020 RS is a commercially available luster pigment with an average particle diameter D50 of about 20 μm obtained by coating glass flakes with a thickness of 1.3 μm with titanium oxide. Their particulate appearances and lustrous appearances, degrees of filter clogging, and foreign substances in coatings also were evaluated. Table 2 also shows the results of the evaluation.

TABLE 2

|  | Example 4 | Example 5 | Example 6 | Comparative Example 1 | Comparative Example 2 |
|---|---|---|---|---|---|
| Average particle diameter D50 (μm) | 24.3 | 22.8 | 21.2 | 22.0 | 20.7 |
| Maximum particle diameter (μm) | 74.0 | 80.7 | 88.0 | 96.0 | 96.0 |
| D90 (μm) | 38.2 | 36.0 | 34.9 | 36.1 | 35.1 |
| D10 (μm) | 15.4 | 13.3 | 11.8 | 11.7 | 10.4 |
| D90/D10 | 2.48 | 2.71 | 2.96 | 3.09 | 3.38 |
| L value | 70.5 | 70.9 | 71.2 | 68.5 | 68.7 |
| Particulate appearance and lustrous appearance | 5 | 5 | 5 | 3 | 3 |
| Filter clogging | 3 | 3 | 3 | 2 | 2 |
| Foreign substances in coating (number of pieces) | 0 | 0 | 0 | 3 | 2 |

In Comparative Examples 1 and 2 whose D90/D10 values were 3.09 and 3.38 and D10 values were 11.7 μm and 10.4 μm respectively, their L values were both about 68. In Examples 4, 5 and 6, D90/D10 values were 2.48, 2.71 and 2.96, and D10 values were 15.4 μm, 13.3 μm and 11.8 μm respectively, and L values were all about 71, which were high values. It is found from these results that the luster pigments of Examples 4 to 6 have higher luminance levels than those of Comparative Examples 1 and 2 because the content of fine particles decreases and the range of particle size distribution is narrowed accordingly. The particulate appearance and lustrous appearance of the luster pigments of Examples 4 to 6 were rated "5", whereas those of Comparative Examples 1 and 2 were rated "3". It is found that the decrease in content of fine particles and the narrower range of particle size distribution result in a significant difference in particulate appearance and lustrous appearance.

As for Comparative Examples 1 and 2 both having a maximum particle diameter of 96.0 μm but having D90 values of 36.1 μm and 35.1 μm respectively, the degrees of their filter clogging were rated "2" as being clogged slightly, and foreign substances also were seen in the coatings. As for Examples 4, 5 and 6 having maximum particle diameters of 74.0 μm, 80.7 μm and 88.0 μm respectively, the degrees of their filter clogging were rated "3" as being not clogged, and no foreign substance was seen in the coatings.

The filter was clogged and foreign substances were seen in the coatings of Comparative Examples 1 and 2 having D90 values of 36.1 μm and 35.1 μm respectively, whereas neither filter clogging nor foreign substances in the coating was seen in Example 4 having a D90 value of 38.2 μm. It is found from these results that the effect of removing coarse particles is reflected in the values of maximum particle diameters rather than the values of D90 and thus the filter clogging and the number of foreign substances in the coatings are improved by adjusting the maximum particle diameters.

Examples 7 and 8, and Comparative Example 3

Glass flakes having a thickness of 1.3 μm were produced in the same manner as in Examples 1 to 3. The glass flakes thus obtained were pulverized using a jet mill type pulverizer so that the glass flakes had an average particle diameter of about 30 μm. Thus, glass flakes (of original flakes) having a D50 value of 30.1 μm, a maximum particle diameter of 114.1 μm, a D90 value of 51.7 μm, a D10 value of 16.1 μm and a D90/D10 value of 3.21 were produced. These glass flakes were sieved for a predetermined time period in the same manner as in Examples 1 to 3 using an upper sieve with a mesh opening of 38 μm, a middle sieve with a mesh opening of 20 μm and a receiving pan on the bottom. Thus, glass flakes of Examples 7 and 8 and Comparative Example 3 were obtained. Table 3 shows the results thereof.

TABLE 3

|  | Original flakes | Example 7 | Example 8 | Comparative Example 3 |
|---|---|---|---|---|
| Sieving time (minutes) | — | 30 | 60 | 90 |
| Average particle diameter D50 (μm) | 30.1 | 32.1 | 30.7 | 31.2 |
| Maximum particle diameter (μm) | 114.1 | 88.0 | 88.0 | 104.7 |
| D90 (μm) | 51.7 | 47.8 | 50.5 | 51.4 |
| D10 (μm) | 16.1 | 22.5 | 18.7 | 17.8 |
| D90/D10 | 3.21 | 2.12 | 2.70 | 2.89 |

As shown in Table 3, the D90/D10 values of Examples 7 and 8 were 2.12 and 2.70 respectively, whereas the D90/D10 value of the original glass flakes was 3.21. The maximum particle diameters of Examples 7 and 8 were both 88.0 μm, whereas the maximum particle diameter of the original glass flakes was 114.1 μm. The D10 values of Examples 7 and 8 were 22.5 μm and 18.7 μm respectively, whereas the D10 value of the original glass flakes was 16.1 μm. It was confirmed that in each of Examples 7 and 8, glass flakes with a narrow range of particle size distribution were obtained.

The D90/D10 value of Comparative Example 3, which differs from Examples 7 and 8 in the sieving time, was 2.89, whereas the D90/D10 value of the original glass flakes was 3.21. The maximum particle diameter of Comparative Example 3 was 104.7 m, whereas the maximum particle diameter of the original glass flakes was 114.1 m. The D10 value of Comparative Example 3 was 17.8 μm, whereas the D10 value of the original glass flakes was 16.1 μm. Thus, it was confirmed that in Comparative Example 3, glass flakes having a D90/D10 value indicating a narrow range of particle size distribution but having a maximum particle diameter that is not necessarily small were obtained.

Examples 9 and 10, and Comparative Examples 4 and 5

As for luster pigments of Examples 9 and 10 and Comparative Example 4 obtained by coating the glass flakes of Examples 7 and 8 and Comparative Example 3 respectively with titanium oxide in the same manner as in Examples 4 and 5, their particle size distributions, L values, particulate appearances and lustrous appearances, degrees of filter clogging, and foreign substances in coatings were evaluated.

Furthermore, as Comparative Example 5, METASHINE (registered trademark) MC 1030 RS (manufactured by Nippon Sheet Glass Co., Ltd.) was evaluated in the same manner. METASHINE (registered trademark) MC 1030 RS is a commercially available luster pigment with an average particle diameter of about 30 μm obtained from a glass flake substrate with a thickness of 1.3 μm. Table 4 shows the evaluation results thereof collectively.

TABLE 4

|  | Example 9 | Example 10 | Comparative Example 4 | Comparative Example 5 |
|---|---|---|---|---|
| Average particle diameter D50 (μm) | 31.9 | 30.9 | 31.5 | 32.0 |
| Maximum particle diameter (μm) | 88.0 | 88.0 | 96.0 | 104.7 |
| D90 (μm) | 47.5 | 50.8 | 51.9 | 54.6 |
| D10 (μm) | 22.2 | 18.8 | 17.9 | 17.2 |
| D90/D10 | 2.14 | 2.70 | 2.90 | 3.17 |
| L value | 71.6 | 72.8 | 72.2 | 68.5 |
| Particulate appearance and lustrous appearance | 5 | 5 | 5 | 4 |
| Filter clogging | 3 | 3 | 2 | 1 |
| Foreign substances in coating (number of pieces) | 0 | 0 | 3 | 5 |

In Comparative Example 5 having a D90/D10 value of 3.17 and a D10 value of 17.2 μm, the L value was about 68. In Examples 9 and 10 having D90/D10 values of 2.14 and 2.70 and D10 values of 22.2 μm and 18.8 μm respectively, the L values were about 72, which were high values. It is found from these results that the decrease in content of fine particles and the narrower range of particle size distribution result in a higher luminance level than that of Comparative Example 5. The particulate appearances and lustrous appearances of Examples 9 and 10 were rated "5", whereas those of Comparative Example 5 were rated "4". It is found from these results that the decrease in content of fine particles and the narrower range of particle size distribution result in such a difference.

As for Comparative Example 5 having a maximum particle diameter of 104.7 μm, the degree of filter clogging was rated "1" as being clogged, and foreign substances also were seen in the coating. As for Examples 9 and 10 both having a maximum particle diameter of 88.0 μm, the degrees of filter clogging both were rated "3" as being not clogged, and no foreign substance was seen in the coatings. It is found that the adjustment of the maximum particle diameters by removing coarse particles improves filter clogging and reduces foreign substances in coatings.

In Comparative Example 4, the L value was about 72, which was a high value, and the particulate appearance and the lustrous appearance were rated "5", which was a comparable level to that of Examples 9 and 10, but the filter clogging was rated "2" as being clogged slightly and foreign substances were seen in the coating. In Comparative Example 4, the D90/D10 value was 2.90, the D10 value was 17.9 μm, and the maximum particle diameter was 96.0 μm. In Examples 9 and 10, the D90/D10 values were 2.14 and 2.70 respectively, the D10 values were 22.2 μm and 18.8 μm respectively, and the maximum particle diameters were both 88.0 μm. As a result of a comparison between Comparative Example 4 and Examples 9 and 10, it is found that it is necessary not only to narrow the range of particle size distribution but also to adjust the maximum particle diameter by removing coarse particles in order to achieve satisfactory levels of all the evaluation items including luminance, particulate appearance, lustrous appearance, filter clogging and foreign substances in coating.

Example 11 and Comparative Example 6

METASHINE (registered trademark) MC 1040 RS (glass flakes coated with titanium oxide) (manufactured by Nippon Sheet Glass Co., Ltd.) was sieved for 30 minutes using an upper sieve with a mesh opening of 45 μm and a lower sieve with a mesh opening of 20 μm respectively. METASHINE (registered trademark) MC 1040 RS is a luster pigment with an average particle diameter of about 40 μm obtained from a glass flake substrate with a thickness of 1.3 μm. The luster pigment thus obtained by sieving was Example 11, and the unsieved luster pigment was Comparative Example 6. Table 5 shows the particle size distributions and L values that were measured respectively, and the evaluation results of particulate appearances and lustrous appearances, degrees of filter clogging and foreign substances in coatings. Judging from their appearances, there was not much difference in particulate appearance because the original glass flakes had a large average particle diameter. However, as for the lustrous appearance, the decrease in content of fine particles and the narrower range of particle size distribution result in reduction of light scattering due to a low content of fine particles and thus a higher rating of Example 11 than Comparative Example 6. This fact can be confirmed because the L value of Example 11 is high. It also can be confirmed that the adjustment of the maximum particle diameter by removing coarse particles improves the filter clogging problem and reduces foreign substances in coating.

TABLE 5

|  | Example 11 | Comparative Example 6 |
|---|---|---|
| Sieving time (minutes) | 30 | — |
| Average particle diameter D50 (μm) | 38.9 | 39.6 |
| Maximum particle diameter (μm) | 88.0 | 124.5 |
| D90 (μm) | 66.6 | 66.9 |
| D10 (μm) | 23.8 | 21.1 |
| D90/D10 | 2.80 | 3.17 |
| L value | 74.2 | 70.2 |
| Particulate appearance and lustrous appearance | 5 | 4-5 |
| Filter clogging | 3 | 1 |
| Foreign substances in coating (number of pieces) | 0 | 7 |

Example 12 and Comparative Example 7

Glass flakes having a thickness of 1.3 μm were produced in the same manner as in Examples 1 to 3. The glass flakes thus obtained were pulverized using a jet mill type pulverizer so that the glass flakes had an average particle diameter of about 10 μm. Thus, glass flakes (original flakes) having a D50 value of 8.5 μm, a maximum particle diameter of 37.0 μm, a D90 value of 15.2 μm, a D10 value of 4.4 μm and a D90/D10 value of 3.45 were produced. These glass flakes were sieved for a predetermined time period in the same manner as in Examples 1 to 3 using an upper sieve with a mesh opening of 25 μm, a middle sieve with a mesh opening of 16 μm and a receiving pan on the bottom. Table 6 shows the results thereof.

TABLE 6

|  | Original flakes | Example 12 | Comparative Example 7 |
|---|---|---|---|
| Sieving time (minutes) | — | 60 | 30 |
| Average particle diameter D50 (μm) | 8.5 | 8.2 | 8.4 |
| Maximum particle diameter (μm) | 37.0 | 33.9 | 33.9 |
| D90 (μm) | 15.2 | 14.0 | 13.3 |
| D10 (μm) | 4.4 | 4.7 | 4.5 |
| D90/D10 | 3.45 | 2.98 | 2.96 |

The following was confirmed from Table 6: The D90/D10 value of Example 12 was 2.98, whereas the D90/D10 value of the original glass flakes was 3.45. The maximum particle diameter of Example 12 was 33.9 μm, whereas the maximum particle diameter of the original glass flakes was 37.0 μm. The D10 value of Example 12 was 4.7 μm, whereas the D10 value of the original glass flakes was 4.4 μm. It was confirmed that in Example 12, glass flakes with a narrow range of particle size distribution were obtained.

The D90/D10 value of Comparative Example 7 was 2.96, whereas the D90/D10 value of the original glass flakes was 3.45. The maximum particle diameter of Comparative Example 7 was 33.9 μm, whereas the maximum particle diameter of the original glass flakes was 37.0 μm. The D10 value of Comparative Example 7 was 4.5 μm, whereas the D10 value of the original glass flakes was 4.4 μm. Thus, it was confirmed that in Comparative Example 7, glass flakes having a D90/D10 value indicating a narrow range of particle size distribution but having a D10 value that is not necessarily large were obtained.

Example 13, and Comparative Examples 8 and 9

Luster pigments were produced, as Example 13 and Comparative Example 8, by coating the glass flakes of Example 12 and Comparative Example 7 respectively with titanium oxide in the same manner as in Examples 4 and 5. As for these luster pigments, the particle size distributions, L values, particulate appearances and lustrous appearances, degrees of filter clogging, and foreign substances in coatings were evaluated.

As Comparative Example 9, a luster pigment produced using the original flakes was evaluated in the same manner. Table 7 shows the evaluation results thereof collectively.

TABLE 7

|  | Example 13 | Comparative Example 8 | Comparative Example 9 |
|---|---|---|---|
| Average particle diameter D50 (μm) | 8.0 | 8.3 | 8.4 |
| Maximum particle diameter (μm) | 33.9 | 33.9 | 37.0 |
| D90 (μm) | 14.2 | 13.2 | 14.8 |
| D10 (μm) | 4.8 | 4.5 | 4.4 |
| D90/D10 | 2.96 | 2.93 | 3.36 |
| L value | 67.1 | 64.4 | 63.8 |
| Particulate appearance and lustrous appearance | 4 | 2 | 1 |
| Filter clogging | 3 | 3 | 3 |
| Foreign substances in coating (number of pieces) | 0 | 0 | 0 |

In Comparative Example 9 having a D90/D10 value of 3.36 and a D10 value of 4.4 μm, the L value was about 64. In Example 13 having a D90/D10 value of 2.96 and a D10 value of 4.8 μm, the L value was about 67, which was a high value. It is found from these results that the decrease in content of fine particles and the narrower range of particle size distribution result in a higher luminance level than that of Comparative Example 9. The particulate appearance and lustrous appearance of Example 13 was rated "4", whereas that of Comparative Example 9 was rated "1". It is found from these results that the decrease in content of fine particles and the narrower range of particle size distribution result in such a difference.

As for Comparative Example 9 having a maximum particle diameter of 37.0 μm and Example 13 having a maximum particle diameter of 33.9 μm, the degrees of filter clogging were both rated "3" as being not clogged, and no foreign substance was seen in the coatings.

In Comparative Example 8, neither filter clogging nor foreign substances in the coating were seen, but the L value was about 64, which was a low value and hardly differed from that of Comparative Example 9. In Comparative Example 8, the D90/D10 value was 2.93, the D10 value was 4.5 μm, and the maximum particle diameter was 33.9 μm. In Example 13, the D90/D10 value was 2.96, the D10 value was 4.8 μm, and the maximum particle diameter was 33.9 μm. As a result of a comparison between them, it is found that it is necessary not only to narrow a range of particle size distribution by adjusting a D90/D10 value but also to adjust a D10 value by removing fine particles in order to achieve satisfactory levels of all the evaluation items including luminance, particulate appearance, lustrous appearance, filter clogging and foreign substances in coating.

Example 14

Glass flakes having a thickness of 0.7 μm were produced in the same manner as in Examples 1 to 3, and the glass flakes thus obtained were pulverized using a jet mill type pulverizer so that the glass flakes had an average particle diameter of about 10 μm. The pulverized glass flakes were sieved for 2 minutes using a single sieve with a mesh opening of 20 μm. Table 8 shows the D50 values, maximum particle diameters, D90 values, D10 values, and D90/D10 values of the original glass flakes and the sieved glass flakes.

TABLE 8

|  | Original flakes | Example 14 |
|---|---|---|
| Sieving time (minutes) | — | 2 |
| Average particle diameter D50 (μm) | 8.3 | 7.9 |
| Maximum particle diameter (μm) | 52.3 | 48.0 |
| D90 (μm) | 14.7 | 13.9 |
| D10 (μm) | 4.5 | 4.7 |
| D90/D10 | 3.27 | 2.96 |

Example 15 and Comparative Example 10

The glass flakes of Example 14 were coated with silver by electroless plating so that the coating had a thickness of about 50 nm. Thus, a luster pigment was produced (Example 15). The unsieved original glass flakes (original flakes shown in Table 8) were coated with silver by electroless plating in the same manner so that the coating had a thickness of about 50 nm. Thus, a luster pigment was produced (Comparative Example 10). Table 9 shows the particle size distributions and L values that were measured respectively, and the evaluation results of particulate appearances and lustrous appearances, degrees of filter clogging and foreign substances in coatings. Table 9 shows that the L value and the particulate appearance and lustrous appearance of the pigment of Example 15 are higher than those of the pigment of Comparative Example 10. Neither filter clogging nor foreign substances in the coatings were seen in both Example 15 and Comparative Example 10.

TABLE 9

|  | Example 15 | Comparative Example 10 |
|---|---|---|
| Average particle diameter D50 (μm) | 8.8 | 8.8 |
| Maximum particle diameter (μm) | 44.0 | 52.3 |
| D90 (μm) | 16.0 | 14.9 |

TABLE 9-continued

|  | Example 15 | Comparative Example 10 |
|---|---|---|
| D10 (μm) | 5.4 | 4.5 |
| D90/D10 | 2.96 | 3.31 |
| L value | 70.0 | 67.1 |
| Particulate appearance and lustrous appearance | 5 | 3 |
| Filter clogging | 3 | 3 |
| Foreign substances in coating (number of pieces) | 0 | 0 |

Example 16 and Comparative Example 11

METASHINE (registered trademark) ME 2040 PS (manufactured by Nippon Sheet Glass Co., Ltd.) that is a metallic luster pigment obtained by coating glass flakes with silver was sieved for 30 minutes using an upper sieve with a mesh opening of 32 μm and a lower sieve with a mesh opening of 20 μm respectively. Thus, a luster pigment of Example 16 was obtained. The unsieved pigment was used as a Comparative Example 11. Table 10 shows the particle size distributions and L values that were measured for respective pigments, and the evaluation results of particulate appearances and lustrous appearances, degrees of filter clogging, and foreign substances in coatings. Table 10 shows that the L value and the particulate appearance and lustrous appearance of the pigment of Example 16 are higher than those of the pigment of Comparative Example 11. Filter clogging and foreign substances in the coating were seen in Comparative Example 11, although Example 16 was free from such problems.

TABLE 10

|  | Example 16 | Comparative Example 11 |
|---|---|---|
| Sieving time (minutes) | 30 | — |
| Average particle diameter D50 (μm) | 34.5 | 33.5 |
| Maximum particle diameter (μm) | 88.0 | 124.5 |
| D90 (μm) | 58.6 | 58.4 |
| D10 (μm) | 20.1 | 15.9 |
| D90/D10 | 2.92 | 3.67 |
| L value | 83.9 | 80.2 |
| Particulate appearance and lustrous appearance | 5 | 4 |
| Filter clogging | 3 | 1 |
| Foreign substances in coating (number of pieces) | 0 | 6 |

Example 17 and Comparative Example 12

An emulsion type mascara was prepared as Example 17 using the following components. The following values are represented by mass percentage.

| (1) hydroxyethyl cellulose | 1.0 |
|---|---|
| (2) methyl p-hydroxybenzoate | 0.2 |
| (3) glycerin | 0.3 |
| (4) polyethylene glycol with high polymerization degree (average molecular weight 2,000,000) | 0.5 |
| (5) purified water | 60.0 |
| (6) luster pigment of Example 11 | 5.0 |
| (7) black iron oxide pigment | 3.0 |
| (8) triethanolamine | 3.0 |
| (9) stearic acid | 5.0 |
| (10) bees wax | 9.0 |
| (11) carnauba wax | 3.0 |
| (12) paraffin wax | 10.0 |

The components (1) to (5) were mixed and evenly dissolved by heating at 75° C. The luster pigment of the component (6) and the black iron oxide pigment of the component (7) were added to the mixture and evenly dispersed through a colloid mill. The component (8) further was mixed, dissolved, and heated at 75° C., and the components (9) to (12) that were heated and evenly melted were added, and the resulting mixture was emulsified and cooled. Thus, an emulsion type mascara was obtained.

An emulsion type mascara of Comparative Example 12 was produced in the same manner as Example 17, except that the luster pigment of Comparative Example 4 was used in place of the luster pigment of the component (6) of Example 17.

Table 11 shows the evaluation results of the particulate appearances and lustrous appearances of Example 17 and Comparative Example 12.

TABLE 11

|  | Example 17 | Comparative Example 12 |
|---|---|---|
| Particulate appearance and lustrous appearance | 5 | 4 |

It is found from the results shown in Table 11 that the emulsion type mascara of Example 17 containing the luster pigment of the present invention is a mascara containing brilliantly glittering particles, compared to the conventional mascara of Comparative Example 12.

Example 18 and Comparative Example 13

An eye shadow was prepared as Example 18 using the following components. The following values are represented by mass percentage.

| (1) talc | 21 |
|---|---|
| (2) muscovite | 20 |
| (3) luster pigment of Example 11 | 40 |
| (4) pigment | 12 |
| (5) squalane | 4 |
| (6) cetyl 2-ethylhexanoate | 1.9 |
| (7) sorbitan sesquioleate | 0.8 |
| (8) preservative | 0.1 |
| (9) fragrance | 0.2 |

The above-mentioned components (1) to (4) were mixed by a Henschel mixer and the components (5) to (9) which were heated and mixed were blown-mixed and then pulverized. The resulting mixture was discharged to a predetermined medium-sized dish. Thus, an eye shadow was obtained.

An eye shadow of Comparative Example 13 was produced in the same manner as Example 18, except that the luster pigment of Comparative Example 4 was used in place of the luster pigment of the component (3) of Example 18

Table 12 shows the evaluation results of the particulate appearances and lustrous appearances of the eye shadows of Example 18 and Comparative Example 13.

TABLE 12

|  | Example 18 | Comparative Example 13 |
|---|---|---|
| Particulate appearance and lustrous appearance | 5 | 4 |

It is found from the results shown in Table 11 that the eye shadow of Example 18 containing the luster pigment of the present invention is an eye shadow containing brilliantly glittering particles, compared to the conventional eye shadow of Comparative Example 13.

Example 19 and Comparative Example 14

A nail polish was prepared as Example 19 using the following components. The following values are represented by mass percentage.

| (1) nitrocellulose | 18.0 |
|---|---|
| (2) toluenesulfonamide resin | 6.0 |
| (3) acetyl tributyl citrate | 6.0 |
| (4) alkyl acrylate copolymer | 2.0 |
| (5) isopropanol | 5.0 |
| (6) benzyldimethylammonium hectorite | 2.0 |
| (7) ethyl acetate | 20.0 |
| (8) butyl acetate | 30.9 |
| (9) prussian blue | 0.1 |
| (10) luster pigment of Example 10 | 10.0 |

After the components (1) to (4) and components (9) and (10) were kneaded by a roller mill, the components (5) to (8) were added thereto, melted, diffused, and evenly dispersed, and then the resulting mixture was filled in a given container. Thus, a nail polish was obtained.

A nail polish was produced as Comparative Example 14 in the same manner as Example 19, except that the luster pigment of Comparative Example 3 was used in place of the luster pigment of the component (10) of Example 19.

Table 13 shows the evaluation results of the particulate appearances and lustrous appearances of the nail polishes of Example 19 and Comparative Example 14.

TABLE 13

|  | Example 19 | Comparative Example 14 |
|---|---|---|
| Particulate appearance and lustrous appearance | 5 | 4 |

It is found from the results shown in Table 13 that the nail polish of Example 19 containing the luster pigment of the present invention is a nail polish containing brilliantly glittering particles, compared to the conventional nail polish of Comparative Example 14.

Example 20 and Comparative Example 15

A lipstick was prepared as Example 20 using the following components. The following values are represented by mass percentage.

| (1) hydrocarbon wax | 20 |
|---|---|
| (2) candelilla wax | 3 |
| (3) glyceryl isostearate | 40 |
| (4) liquid paraffin | 26.8 |
| (5) titanium dioxide | 4 |
| (6) luster pigment of Example 16 | 0.2 |
| (7) organic pigment | 5.8 |
| (8) fragrance | 0.2 |

The above-mentioned components (1) to (4) were dissolved at 85° C. and the components (5) to (7) were added thereto. The resulting mixture was stirred and mixed, and after that, the component (8) was further added thereto and stirred, and the resulting mixture was filled in a given container. Thus, a lipstick was obtained.

A lipstick of Comparative Example 15 was produced in the same manner as Example 20, except that the luster pigment of Comparative Example 11 was used in place of the luster pigment of the component (6) of Example 20.

Table 14 shows the evaluation results of the particulate appearances and lustrous appearances of Example 20 and Comparative Example 15.

TABLE 14

|  | Example 20 | Comparative Example 15 |
|---|---|---|
| Particulate appearance and lustrous appearance | 5 | 4 |

It is found from the results shown in Table 14 that the lipstick of Example 20 containing the luster pigment of the present invention is a lipstick containing brilliantly glittering particles, compared to the conventional lipstick of Comparative Example 15.

Example 21 and Comparative Example 16

A coating composition was prepared as Example 21 using the following components. The following values are represented by mass percentage.

First, the following components were dispersed for 60 minutes using a paint shaker to produce a dispersion vehicle.

| (1) alkyd resin type varnish | 20.6 |
|---|---|
| (2) melamine resin type varnish | 10.6 |
| (3) Swazol | 15.6 |
| (4) luster pigment of Example 5 | 15.6 |
| The following components further were added to and mixed with the above dispersion vehicle. | |
| (5) alkyd resin type varnish | 26.3 |
| (6) melamine resin type varnish | 11.3 |

Thus, a coating composition was produced.

A coating composition of Comparative Example 16 was produced in the same manner as Example 21, except that the luster pigment of Comparative Example 1 was used in place of the luster pigment of the component (4) of Example 21.

The particulate appearances and lustrous appearances of the coating compositions of Example 21 and Comparative Example 16 were evaluated respectively. Table 15 shows the results thereof.

TABLE 15

|  | Example 21 | Comparative Example 16 |
|---|---|---|
| Particulate appearance and lustrous appearance | 5 | 3 |

It is found from the results shown in Table 15 that the coating composition of Example 21 containing the luster pigment of the present invention is a glittering coating product with particulate appearance, compared to the conventional coating composition of Comparative Example 16. In addition, since the coating composition of Example 21 contains the luster pigment of the component (4) having a low content of coarse particles, filter clogging can be reduced when filtering, compared to the coating composition of Comparative Example 16.

Example 22 and Comparative Example 17

98% by mass of methyl methacrylate copolymer beads and 2% by mass of the luster pigment of Example 6 were mixed and stirred by a Henschel mixer to obtain a resin composition of Example 22. An acrylic resin molded product of 0.5 mm in thickness was produced from this resin composition using an extruder.

A resin composition of Comparative Example 17 was produced in the same manner as Example 22, except that the luster pigment of Comparative Example 2 was used in place of the luster pigment of Example 22. An acrylic resin molded product of 0.5 mm in thickness was produced from this resin composition.

Table 16 shows the evaluation results of the particulate appearances and lustrous appearances of the resin molded products of Example 22 and Comparative Example 17.

TABLE 16

|  | Example 22 | Comparative Example 17 |
|---|---|---|
| Particulate appearance and lustrous appearance | 5 | 3 |

It is shown from the results shown in Table 16 that the resin molded product of Example 22 containing the luster pigment of the present invention exhibits a color tone that is rich in particulate appearance and lustrous appearance, compared to the conventional resin molded product of Comparative Example 17.

Example 23 and Comparative Example 18

An ink was prepared as Example 23 by mixing the following components sufficiently. The following values are represented by mass percentage.

| (1) luster pigment of Example 9 | 12 |
|---|---|
| (2) ketone resin | 19 |
| (3) ethanol | 59 |
| (4) propylene glycol monomethyl ether | 10 |

An ink composition of Comparative Example 18 was produced in the same manner as Example 23, except that the luster pigment of Comparative Example 5 was used in place of the luster pigment of the component (1) in the ink composition of Example 23.

The particulate appearances and lustrous appearances of the ink compositions of Example 23 and Comparative Example 18 were evaluated respectively by writing on white paper with the ink compositions of Example 23 and Comparative Example 18. Table 17 shows the results thereof.

TABLE 17

|  | Example 23 | Comparative Example 18 |
|---|---|---|
| Particulate appearance and lustrous appearance | 5 | 3 |

It is shown from the results shown in Table 17 that the ink composition of Example 23 containing the luster pigment of the present invention imparts a color tone having a particulate appearance and a very beautiful lustrous appearance to the handwriting, compared to the conventional ink composition of Comparative Example 18.

Example 24 and Comparative Example 19

A powder foundation was prepared as Example 24 using the following components. The following values are represented by mass percentage.

| (1) flaky particles of Example 1 | 35 |
|---|---|
| (2) talc | 20 |
| (3) glass flakes coated with titanium | 20 |
| (4) titanium dioxide | 10 |
| (5) spherical polyethylene powder | 5 |
| (6) red iron oxide | 1 |
| (7) yellow iron oxide | 3 |
| (8) black iron oxide | 0.1 |
| (9) silicone oil | 1 |
| (10) 2-ethylhexyl palmitate | 9 |
| (11) sorbitan sesquioleate | 1 |
| (12) preservative | 0.3 |
| (13) fragrance | 0.1 |

The components (1) to (8) were mixed by a Henschel mixer. To this mixture, the components (9) to (13) dissolved and mixed by heat were added and then pulverized by a pulverizer. The resultant powder was molded into a plate of 6 cm in diameter at a pressure of (1.5 kg/cm$^2$). Thus, a powder foundation was produced.

A powder foundation of Comparative Example 19 was produced in the same manner as Example 24, except that the flaky particles of original flakes were used in place of the flaky particles of the component (1) of Example 24.

For the sensory evaluation test, the following five-point scale was used. Ten panelists were employed, and the translucency of the foundations was evaluated based on the average value of the evaluation points of these ten panelists.

(Evaluation Standards)

1: Not translucent, dull

2: Not so translucent, slightly dull

3: Moderately translucent

4: Fairly translucent

5: Highly translucent

Table 18 shows the evaluation results of the translucency of the powder foundations of Example 24 and Comparative Example 19.

TABLE 18

|  | Example 24 | Comparative Example 19 |
|---|---|---|
| Translucency | 5 | 3.8 |

As for the powder foundation of Example 24, all the ten panelists rated "5", and thus the average value of evaluation was "5". On the other hand, as for the powder foundation of Comparative Example 19, eight panelists rated "4" and two panelists rated "2", and thus the average value of evaluation was "3.8". It is found from these results that the powder foundation of Example 24 containing the flaky particles of the present invention has a higher translucency than the conventional powder foundation of Comparative Example 19.

INDUSTRIAL APPLICABILITY

Since the flaky particles and pigment of the present invention can realize a highly particulate appearance and a highly lustrous appearance, they can be used suitably as a filler for imparting a lustrous appearance to cosmetics, coating compositions, resin compositions, ink compositions and the like. Furthermore, since the cosmetic, coating composition, resin composition and ink composition of the present invention each have a highly lustrous appearance and a highly particulate appearance, they can be used suitably for products required to have a quality appearance, for example.

The invention claimed is:

1. Flaky particles, the flaky particles being made of glass, wherein the flaky particles have a particle size distribution in which a value of D90/D10 is at least 2.0 but not more than 3.0, a value of D10 is at least 4.7 μm but not more than 25 μm, and a maximum particle diameter is 90 μm or less, where D10 is defined as a particle diameter at which a cumulative volume of particles reaches 10% when counted from the smaller side, and D90 is defined as a particle diameter at which a cumulative volume of particles reaches 90% when counted from the smaller side.

2. A luster pigment comprising: flaky particles; and at least one layer selected from the group consisting of a metallic layer and a metallic oxide layer that are formed on at least a part of a surface of each of the flaky particles,
wherein the flaky particles are made of glass, and
the luster pigment has a particle size distribution in which a value of D90/D10 is at least 2.0 but not more than 3.0, a value of D10 is at least 4.7 μm but not more than 25 and a maximum particle diameter is 90 μm or less, where D10 is defined as a particle diameter at which a cumulative volume of particles reaches 10% when counted from the smaller side, and D90 is defined as a particle diameter at which a cumulative volume of particles reaches 90% when counted from the smaller side.

3. The luster pigment according to claim 2,
wherein the flaky particles have a particle size distribution in which a value of D90/D10 is at least 2.0 but not more than 3.0, a value of D10 is at least 4.7 μm but not more than 25 μm, and a maximum particle diameter is 90 μm or less, where D10 is defined as a particle diameter at which a cumulative volume of particles reaches 10% when counted from the smaller side, and D90 is defined as a particle diameter at which a cumulative volume of particles reaches 90% when counted from the smaller side.

4. A cosmetic comprising the flaky particles according to claim 1.

5. A coating composition comprising the flaky particles according to claim 1.

6. A resin composition the flaky particles according to claim 1.

7. An ink composition comprising the flaky particles according to claim 1.

8. A cosmetic comprising the luster pigment according to claim 2.

9. A coating composition comprising the luster pigment according to claim 2.

10. A resin composition comprising the luster pigment according to claim 2.

11. An ink composition comprising the luster pigment according to claim 2.

* * * * *

UNITED STATES PATENT AND TRADEMARK OFFICE
CERTIFICATE OF CORRECTION

| | | |
|---|---|---|
| PATENT NO. | : 8,926,746 B2 | Page 1 of 1 |
| APPLICATION NO. | : 12/225907 | |
| DATED | : January 6, 2015 | |
| INVENTOR(S) | : Wakamiya | |

It is certified that error appears in the above-identified patent and that said Letters Patent is hereby corrected as shown below:

Title Page 2, Item "56", column 2, under "Other Publications", line 4, insert -- Daikuhara, Daiji, Examiner, -- before "Japanese".

In the Specification

Column 2, line 37, delete "25 g/m," and insert -- 25 μm, --.

Column 9, line 20, delete "+200 mm" and insert -- Φ200 mm --.

Column 14, line 40, delete "104.7 m," and insert -- 104.7 μm, --.

Column 14, line 41, delete "114.1 m." and insert -- 114.1 μm. --.

In the Claims

Column 26, line 8, in Claim 2, delete "25" and insert -- 25 μm, --.

Column 26, line 29, in Claim 6, after "composition" insert -- comprising --.

Signed and Sealed this
Fifteenth Day of September, 2015

Michelle K. Lee
*Director of the United States Patent and Trademark Office*